United States Patent [19]

Baumgarth et al.

[11] Patent Number: 4,931,454
[45] Date of Patent: Jun. 5, 1990

[54] AZACHROMAN DERIVATIVES WITH EFFECTS ON THE CARDIOVASCULAR SYSTEM

[75] Inventors: Manfred Baumgarth, Darmstadt; Rolf Gericke, Seeheim; Ingeborg Lues, Darmstadt; Jacques De Peyer, Seeheim; Rolf Bergmann, Reichelsheim, all of Fed. Rep. of Germany

[73] Assignee: Merck Patent Gesellschaft mit beschrankter Haftung, Darmstadt, Fed. Rep. of Germany

[21] Appl. No.: 248,502

[22] Filed: Sep. 23, 1988

[30] Foreign Application Priority Data

Sep. 24, 1987 [DE] Fed. Rep. of Germany ....... 3732146

[51] Int. Cl.$^5$ ................ A61K 31/495; A61K 31/505; C07D 491/052
[52] U.S. Cl. .................................. 514/254; 514/274; 514/302; 544/238; 544/310; 544/316; 544/405; 546/15; 546/115; 546/116
[58] Field of Search ............... 546/115, 15, 116; 514/254, 274, 302; 544/238, 310, 316, 405

[56] References Cited

U.S. PATENT DOCUMENTS 4,812,459 3/1989 Evans et al. .................. 514/302

FOREIGN PATENT DOCUMENTS 0205292 12/1986 European Pat. Off. .
WO87/07607 12/1987 PCT Int'l Appl. .

OTHER PUBLICATIONS

CA 109: 222477u, Edwin, Synergistic Antihypertensives, 6/15/88, 26 pages.

Primary Examiner—Richard A. Schwartz
Assistant Examiner—Catherine S. Kilby Scalzo
Attorney, Agent, or Firm—Millen, White & Zelano

[57] ABSTRACT

An azachroman derivative of the formula

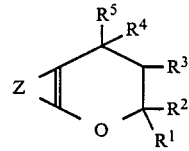

wherein
Z is
 (a) —N=CH—CH=CH—,
 (b) —CH=N—CH=CH—,
 (c) —CH=CH—N=CH— or
 (d) —CH=CH—CH=N—;
$R^1$ is A,
$R^2$ is H or A, or
$R^1$ and $R^2$ together are alkylene with 3–6 C atoms;
$R^3$ is OH or OAc,
$R^4$ is H, or
$R^3$ and $R^4$ together are a bond;
$R^5$ is 1H-2-pyridon-1-yl, 1H-6-pyridazinon-1-yl, 1H-2-pyrimidinon-1-yl, 1H-6-pyrimidinon-1-yl, 1H-2-pyrazinon-1-yl or 1H-2-thiopyridon-1-yl, or 1H-2-pyridon-1-yl, 1H-6-pyridazinon-1-yl, 1H-2-pyrimidinon-1-yl, 1H-6-pyrimidinon-1-yl, 1H-2-pyrazinon-1-yl or 1H-2-thiopyridon-1-yl mono- or disubstituted by A, F, Cl, Br, I, OH, OA, OAc, $NO_2$, $NH_2$, AcNH, HOOC or AOOC;
A is $C_{1-6}$-alkyl and
Ac is $C_{1-18}$-alkanoyl or $C_{7-11}$-aroyl;
or a pharmaceutically acceptable salt thereof is claimed. This compound exhibits vasodilatory and anti-hypertensive effects and is suitable for the treatment of alopecia.

14 Claims, No Drawings

AZACHROMAN DERIVATIVES WITH EFFECTS ON THE CARDIOVASCULAR SYSTEM

SUMMARY OF THE INVENTION

The invention relates to new azachroman derivatives of the formula I

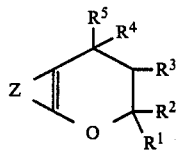

wherein
Z is
(a) —N=CH—CH=CH—,
(b) —CH=N—CH=CH—,
(c) —CH=CH—N=CH— or
(d) —CH=CH—CH=N—,
$R^1$ is A,
$R^2$ is H or A,
$R^1$ and $R^2$ together are also alkylene with 3–6 C atoms,
$R^3$ is OH or OAc,
$R^4$ is H,
$R^3$ and $R^4$ together are also a bond,
$R^5$ is a 1H-2-pyridon-1-yl, 1H-6-pyridazinon-1-yl, 1H-2-pyrimidinon-1-yl, 1H-6-pyrimidinon-1-yl, 1H-2-pyrazinon-1-yl or 1H-2-thiopyridon-1-yl radical which is unsubstituted or mono- or disubstituted by A, F, Cl, Br, I, OH, OA, OAc, $NO_2$, $NH_2$, AcNH, HOOC and/or AOOC, it also being possible for these radicals to be partly hydrogenated,
A is alkyl with 1–6 C atoms and
Ac is alkanoyl with 1–8 C atoms or aroyl with 7–11 C atoms,
and salts thereof.

Azachroman compounds are known from European Patent A1-205,292.

DETAILED DISCUSSION

The invention has as an object discovering new compounds with useful properties, in particular those which can be used for the preparation of medicaments.

Upon further study of the specification and appended claims, further objects and advantages of this invention will become apparent to those skilled in the art.

These objects have been satisfied by providing compounds of the formula

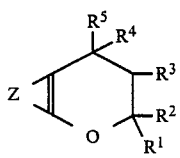

wherein
Z is
(a) —N=CH—CH=CH—,
(b) —CH=N—CH=CH—,
(c) —CH=CH—N=CH— or
(d) —CH=CH—CH=N—;
$R^1$ is A,
$R^2$ is H or A, or
$R^1$ and $R^2$ together are alkylene with 3–6 C atoms;
$R^3$ is OH or OAc,
$R^4$ is H, or
$R^3$ and $R^4$ together are a bond;
$R^5$ is 1H-2-pyridon-1-yl, 1H-6-pyridazinon-1-yl, 1H-2-pyrimidinon-1-yl, 1H-6-pyrimidinon-1-yl, 1H-2-pyrazinon-1-yl or 1H-2-thiopyridon-1-yl, or 1H-2-pyridon-1-yl, 1H-6-pyridazinon-1-yl, 1H-2-pyrimidinon-1-yl, 1H-6-pyrimidinon-1-yl, 1H-2-pyrazinon-1-yl or 1H-2-thiopyridon-1-yl mono- or disubstituted by A, F, Cl, Br, I, OH, OA, OAc, $NO_2$, $NH_2$, AcNH, HOOC or AOOC;
A is $C_{1-6}$-alkyl and
Ac is $C_{1-8}$-alkanoyl or $C_{7-11}$-aroyl; or a pharmaceutically acceptable salt thereof. Partially hydrogenated $R^5$ radicals include those above where one double bond has been hydrogenated, said radicals having at least one double bond.

It has been found that the compounds of the formula I and their physiologically acceptable salts have useful pharmacological properties, coupled with a good tolerability. Thus, they exhibit effects on the cardiovascular system, and as a rule a selective attack on the coronary system can be observed at lower doses and an antihypertensive effect at higher doses. On the coronary system, for example, a decrease in resistance and increase in flow occur, i.e., a vasodilatory effect is achieved, the influence on the heart rate remaining low. The compounds moreover exhibit a relaxing effect on various smooth muscle organs (gastrointestinal tract, respiratory system and uterus). The effects of the compounds can be determined with the aid of methods which are known per se, such as are described, for example, in European Patent A1-76,075, European Patent A1-173,848 or Australian Patent A-45,547/85 (Derwent Farmdoc No. 86081769) and by K. S. Meesmann et al., Arzneimittelforschung 25 (11), 1975, 1770–1776. Examples of suitable experimental animals are mice, rats, guinea-pigs, dogs, cats, monkeys and pigs.

The compounds can therefore be used as medicament active compounds in human and veterinary medicine. They can furthermore be used as intermediates for the preparation of other medicament active compounds.

The compounds of the formula I include:
(a) the 5-azachroman derivatives of the formula Ia (=I, wherein Z is —N=CH—C=CH—; 2H-pyrano[3,2-b]pyridines and 3,4-dihydro derivatives thereof);
(b) the 6-azachroman derivatives of the formula Ib (=I, wherein Z is —CH=N—CH=CH—; 2H-pyrano[3,2-c]pyridines and 3,4-dihydro derivatives thereof; ring index No. 1698);
(c) the 7-azachroman derivatives of the formula Ic (=I, wherein Z is —CH=CH—N=CH—; 2H-pyrano[2,3-c]pyridines and 3,4-dihydro derivatives thereof);
(d) the 8-azachroman derivatives of the formula Ic (=I, wherein Z is —CH=CH—CH=N—; 2H-pyrano[2,3-d]pyridines and 3,4-dihydro derivatives thereof; ring index No. 1701).

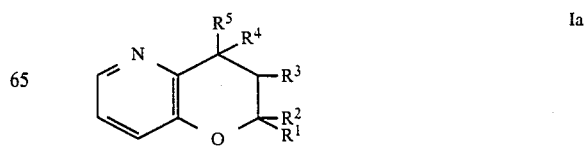

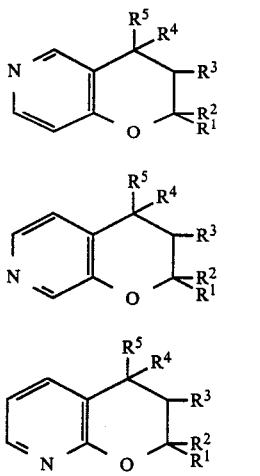

The compounds of the formula Ib are preferred.

In the formulae shown, A is a preferably straight-chain alkyl group with 1–6, preferably 1–4 and in particular 1, 2 or 3, C atoms, and specifically preferably methyl, and furthermore preferably ethyl, propyl, isopropyl, butyl or isobutyl, and moreover preferably sec.-butyl, tert.-butyl, pentyl, isopentyl (3-methylbutyl), hexyl or isohexyl (4-methylpentyl).

If $R^1$ and $R^2$ together are alkylene, the alkylene group is preferably straight-chain, and specifically preferably $-(CH_2)_n-$, wherein n is 3, 4, 5 or 6.

Ac is preferably alkanoyl with 1–6, in particular 1, 2, 3 or 4, C atoms, and specifically preferably formyl or acetyl, and moreover preferably propionyl, butyryl, isobutyryl, pentanoyl or hexanoyl, and furthermore preferably banzoyl, o-, m- or p-toluyl or 1- or 2-naphthoyl.

$R^1$ and $R^2$ are preferably each alkyl, in particular each methyl or ethyl, and preferably each methyl.

$R^3$ and $R^4$ are preferably together a bond. If $R^4$ is H, $R^3$ is preferably OH, O—CHO or O—COCH$_3$.

$R^5$ is preferably unsubstituted 1H-2-pyridon-1-yl, 1H-2-pyrazinon-1-yl or 1H-4-hydroxy-2-pyridon-1-yl, and furthermore preferably unsubstituted 1H-6-pyridazinon-1-yl, 4,5-dihydro-1H-6-pyridazinon-1-yl, 1H-2-pyrimidinon-1-yl, 1H-6-pyrimidinon-1-yl or 1H-2-thiopyridon-1-yl. If $R^5$ is a substituted pyridone or thiopyridone ring, this ring is preferably monosubstituted in the 3-, 4- or 5-position or disubstituted in the 3- and 5-position. Particularly preferred substituents are OH, NO$_2$ and NH$_2$, and furthermore AOOC, OA, Cl, Br and NHCOCH$_3$, and particularly preferred substituted radicals $R^5$ are specifically 4- and furthermore 3-, 5- and 6-hydroxy-, 3-, 4-, 5- or 6-methoxy-, 3-, 4-, 5- or 6-acetoxy-, 3-, 5- or 6-chloro-, 3- or 5-nitro-, 3- or 5-amino-, 3- or 5-carboxy-, 3- or 5-methoxycarbonyl-, 3- or 5-ethoxycarbonyl-, 3- or 5-acetamido-, 3,5-dichloro-, 3,5-dibromo-, 3-chloro-5-nitro-, 3-nitro-5-chloro-, 3-bromo-5-nitro-, 3-nitro-5-bromo-, 3,5-dinitro-, 3-chloro-5-amino-, 3-amino-5-chloro-, 3-bromo-5-amino-, 3-amino-5-bromo-, 3-chloro-5-acetamido-, 3-acetamido-5-chloro-, 3-bromo-5-acetamido- or 3-acetamido-5-bromo-1H-2-pyridon-1-yl or -1H-2-thiopyridon-1-yl, 1H-3-, 1H-4- or 1H-5-hydroxy-6-pyridazinon-1-yl, 1H-3-, 1H-4- or 1H-5-ethoxycarbonyl-6-pyridazinon-1-yl, 1H-4-, 1H-5- or 1H-6-hydroxy-2-pyrimidinon-1-yl or 1H-2- or 1H-4-hydroxy-6-pyrimidinon-1-yl.

$R^5$ can furthermore preferably be: 3,4-dihydro-1H-2-pyridon-1-yl, 2,3-dihydro-6H-2-pyridon-1-yl, 5,6-dihydro-1H-2-pyridon-1-yl, 2,3-dihydro-1H-6-pyridazinon-1-yl, 1,2-dihydro-5H-6-pyridazinon-1-yl, 3,4-dihydro-1H-2-pyrimidinon-1-yl, 1,6-dihydro-3H-2-pyrimidinon-1-yl, 5,6-dihydro-1H-2-pyrimidinon-1-yl, 2,3-dihydro-1H-6-pyrimidinon-1-yl, 1,2-dihydro-5H-6-pyrimidinon-1-yl, 4,5-dihydro-1H-6-pyrimidinon-1-yl, 3,4-dihydro-1H-2-pyrazinon-1-yl, 1,6-dihydro-3H-2-pyrazinon-1-yl, 5,6-dihydro-1H-2-pyrazinon-1-yl, 3,4-dihydro-1H-2-thiopyridon-1-yl, 2,3-dihydro-6H-2-thiopyridon-1-yl or 5,6-dihydro-1H-2-thiopyridon-1-yl.

The invention accordingly particularly relates to those compounds of the formulae I, Ia, Ib, Ic and Id in which at least one of the radicals mentioned has one of the abovementioned preferred meanings. Some preferred groups of compounds can be expressed by the following formulae Ie to Im and Iae to Iam, Ibe to Ibm, Ice to Icm and Ide to Idm, which correspond to the formulae I, Ia, Ib, Ic and Id and wherein the radicals not described in more detail have the meaning given in the case of these formulae, but wherein in Ie, Iae, Ibe, Ice and Ide $R^1$ and $R^2$ are each A;

in If, Iaf, Ibf, Icf and Idf $R^1$ and $R^2$ are each CH$_3$;

in Ig, Iag, Ibg, Icg and Idg $R^1$ and $R^2$ together are alkylene with 3–6 C atoms;

in Ih, Iah, Ibh, Ich and Idh $R^5$ is 1H-2-pyridon-1-yl, 1H-2-pyrazinon-1-yl, 1H-6-pyridazinon-1-yl, 4,5-dihydro-1H-6-pyridazinon-1-yl, 1H-2-pyrimidinon-1-yl, 1H-6-pyrimidinon-1-yl, 1H-2-thiopyridon-1-yl, 3-, 4-, 5- or 6-hydroxy-, 3-, 4-, 5- or 6-methoxy-, 3-, 4-, 5- or 6-acetoxy-, 3-, 5- or 6-chloro-, 3- or 5-nitro-, 3- or 5-amino-, 3- or 5-carboxy-, 3- or 5-methoxycarbonyl-, 3- or 5-ethoxycarbonyl-, 3- or 5-acetamido-, 3,5-dichloro-, 3,5-dibromo-, 3-chloro-5-nitro-, 3-nitro-5-chloro-, 3-bromo-5-nitro-, 3-nitro-5-bromo-, 3,5-dinitro-, 3-chloro-5-amino, 3-amino-5-chloro-, 3-bromo-5-amino-, 3-amino-5-bromo-, 3-chloro-5-acetamido-, 3-acetamido-5-chloro-, 3-bromo-5-acetamido- or 3-acetamido-5-bromo-1H-2-pyridon-1-yl or -1H-2-thiopyridon-1-yl, 1H-3-, 1H-4- or 1H-5-hydroxy-6-pyridazinon-1-yl, 1H-3-, 1H-4- or 1H-5-ethoxycarbonyl-6-pyridazinon-1-yl, 1H-4-, 1H-5- or 1H-6-hydroxy-2-pyrimidinon-1-yl or 1H-2- or 1H-4-hydroxy-6-pyrimidinon-1-yl;

in Ii, Iai, Ibi, Ici and Idi $R^5$ is 1H-2-pyridon-1-yl, 1H-2-pyrazinon-1-yl or 1H-4-hydroxy-2-pyridon-1-yl;

in Ij, Iaj, Ibj, Icj and Idj $R^5$ is 1H-2-pyridon-1-yl;

in Ik, Iak, Ibk, Ick and Idk $R^1$ and $R^2$ are each CH$_3$ and $R^5$ is 1H-2-pyridon-1-yl, 1H-2-pyrazinon-1-yl, 1H-6-pyridazinon-1-yl, 4,5-dihydro-1H-6-pyridazinon-1-yl, 1H-2-pyrimidinon-1-yl, 1H-6-pyrimidinon-1-yl, 1H-2-thiopyridon-1-yl, 3-, 4-, 5- or 6-hydroxy, 3-, 4-, 5- or 6-methoxy-, 3-, 4-, 5- or 6-acetoxy-, 3-, 5- or 6-chloro-, 3- or 5-nitro-, 3- or 5-amino-, 3- or 5-carboxy-, 3- or 5-methoxycarbonyl-, 3- or 5-ethoxycarbonyl-, 3- or 5-acetamido-, 3,5-dichloro-, 3,5-dibromo-, 3-chloro-5-nitro-, 3-nitro-5-chloro-, 3-bromo-5-nitro-, 3-nitro-5-bromo-, 3,5-dinitro-, 3-chloro-5-amino-, 3-amino-5-chloro-, 3-bromo-5-amino-, 3-amino-5-bromo-, 3-chloro-5-acetamido-, 3-acetamido-5-chloro-, 3-bromo-5-acetamido- or 3-acetamido-5-bromo-1H-2-pyridon-1-yl or -1H-2-thiopyridon-1-yl, 1H-3, 1H-4- or 1H-5-hydroxy-6-pyridazinon-1-yl, 1H-3-, 1H-4- or 1H-5-ethoxycarbonyl-6-pyridazinon-1-yl, 1H-4-, 1H-5- or 1H-6-hydroxy-2-pyrimidinon-1-yl or 1H-2- or 1H-4-hydroxy-6-pyrimidinon-1-yl;

in Il, Ial, Ibl, Icl and Idl and $R^1$ and $R^2$ are each $CH_3$ and $R^5$ is 1H-2-pyridon-1-yl, 1H-2-pyrazinon-1-yl or 1H-4-hydroxy-2-pyridon-1-yl;

and in Im, Iam, Ibm, Icm and Idm $R^1$ and $R^2$ are each $CH_3$ and $R^5$ is 1H-2-pyridon-1-yl.

Compounds of the formulae I′ and Ia′ to Im′, Iae′ to Iam′, Ibe′ to Ibm′, Ice′ to Icm′ and Ide′ to Idm′, which correspond to the formulae I and Ia to Im, Iae to Iam, Ibe to Ibm, Ice to Icm and Ide to Idm, but wherein in each case additionally $R^3$ is OH, OCHO or $OCOCH_3$ and $R^4$ is H, are furthermore preferred.

Compounds of the formulae I″ and Ia″ to Im″, Iae″ to Iam″, Ibe″ to Ibm″, Ice″ to Icm″ and Ide″ to Idm″, which correspond to the formulae I and Ia to Im, Iae to Iam, Ibe to Ibm, Ice to Icm and Ide to Idm, but wherein in each case additionally $R^3$ and $R^4$ together are a bond, are furthermore preferred.

The radicals $R^1$ to $R^5$, A and Ac otherwise have the meanings described above and below in the case of formula I, unless expressly stated differently.

The invention furthermore relates to a process for the preparation of azachroman derivatives of the formula I, characterized in that a 3,4-epoxy-azachroman of the formula II

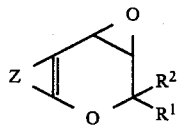
II wherein $R^1$, $R^2$ and Z have the meaning given in the case of formula I, is reacted with a compound of the formula III $R^5$—H          III wherein $R^5$ has the meaning given in the case of formula I, or with one of its reactive derivatives, or that an N-oxide which otherwise corresponds to formula I is reduced, and/or in that a compound of the formula I wherein $R^3$ is OH and $R^4$ is H is dehydrated and/or in that one or more of the radicals $R^3$ and/or $R^5$ in a compound of the formula I is/are converted into other radicals $R^3$ and/or $R^5$, and/or in that a basic compound of the formula I is converted into one of its acid addition salts by treatment with an acid.

The compounds of the formula I are otherwise prepared by methods which are known per se, such as are described in the literature (for example in the standard works, such as Houben-Weyl, Methoden der organischen Chemie (Methods of Organic Chemistry), Georg-Thieme-Verlag, Stuttgart; Organic Reactions, John Wiley & Sons, Inc., New York; and in the abovementioned patent applications), and in particular under reaction conditions which are known and suitable for the reactions mentioned. Variants which are known per se and are not mentioned here in more detail can also thereby be utilized.

If desired, the starting substances can also be formed in situ such that they are not isolated from the reaction mixture but are immediately reacted further to give the compounds of the formula I.

The compounds of the formula I are preferably prepared by reaction of compounds of the formula II with compounds of the formula III, advantageously in the presence of an inert solvent at temperatures between about 0° and 150°.

The starting substances II are known in some cases, and those of the formula III are as a rule known. Where they are not known, they can be prepared by methods which are known per se. Thus, the starting substances of the formula II are obtainable by reaction of propargyl chlorides of the formula $HC{\equiv}C-CR^1R^2-Cl$ with hydroxypyridines of the formula

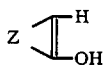

to give the phenol ethers of the formula

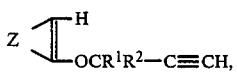

cyclization to give azachromenes corresponding to the formula I wherein $R^3$ and $R^4$ together are a bond but $R^5$ is replaced by an H atom, addition of HOBr to give the bromohydrin (IV) corresponding to formula I wherein $R^3$ is OH but $R^4$ is replaced by Br and $R^5$ is replaced by H, and dehydrobromination (for the method, compare, for example, European Patent A1-205,292).

To prepare the epoxides of the formula II, it is also possible to react 2-hydroxy-3-, -4-, -5- or -6-azaacetophenone with a carbonyl compound of the formula $R^1$-CO-$R^2$ to give 2-$R^1$-2-$R^2$-5-, -6-, -7- or -8-azachroman-4-one, subsequently to reduce this to 2-$R^1$-2-$R^2$-5-, -6-, -7- or -8-azachroman-4-ol, to dehydrate this to give the corresponding 2-$R^1$-2-$R^2$-5-, -6-, -7- or -8-aza-2H-chromenes and to react these further to give the 2-$R^1$-2-$R^2$-5-, -6-, -7- or -8-aza-3,4-epoxy-chroman.

Suitable reactive derivatives of III are the corresponding salts, for example the Na or K salts, which can also be formed in situ.

It is advantageous to work in the presence of a base. Examples of suitable bases are alkali metal or alkaline earth metal hydroxides, hydrides or amides, such as NaOH, KOH, $Ca(OH)_2$, NaH, KH, $CaH_2$, $NaNH_2$ or $KNH_2$, and furthermore organic bases, such as triethylamine or pyridine, which can also be used in excess and can then simultaneously serve as the solvent.

Suitable inert solvents are, in particular, alcohols, such as methanol, ethanol, isopropanol, n-butanol or tert.-butanol; ethers, such as diethyl ether, diisopropyl ether, tetrahydrofuran or dioxane; glycol ethers, such as ethylene glycol monomethyl or monoethyl ether (methylglycol or ethylglycol) or ethylene glycol dimethyl ether (diglyme); ketones, such as acetone or butanone; nitriles, such as acetonitrile; nitro compounds, such as nitromethane or nitrobenzene; esters, such as ethyl acetate; amides, such as dimethylformamide (DMF), dimethylacetamide or phosphoric acid hexamethyltriamide; sulfoxides, such as dimethyl sulfoxide (DMSO); chlorinated hydrocarbons, such as methylene chloride, chloroform, trichloroethylene, 1,2-dichloroethane or carbon tetrachloride; and hydrocarbons, such as benzene, toluene or xylene. Mixtures of these solvents with one another are furthermore suitable.

The epoxide II can also be prepared in situ, for example by the action of a base on the corresponding bromohydrin IV.

The compounds of formula I can also be manufactured by reduction of the corresponding N-oxides, f.e., with hexachlorodisilane in chloroform at temperatures between −10° and +40°. The N-oxides can, e.g., be obtained by reacting the N-oxides of the epoxides of formula II with compounds of formula III.

A compound of the formula I wherein $R^3$ is OH and $R^4$ is H can be converted into a compound of the formula I wherein $R^3$ and $R^4$ together are a bond by treatment with a dehydrating agent. This is effected, for example, by the action of one of the bases mentioned, for example NaH, in one of the solvents mentioned, for example DMSO, at temperatures between 0° and 150°.

One or more of the radicals $R^3$ and/or $R^5$ in a compound of the formula I can furthermore be converted into other radicals $R^3$ and/or $R^5$.

For example, it is possible for an H atom to be replaced by a halogen atom by means of halogenation or by a nitro group by means of nitration and/or for a nitro group to be reduced to an amino group and/or for an amino or hydroxyl group to be alkylated or acylated and/or for a substituted or unsubstituted 1H-2-pyridon-1-yl radical to be converted into the corresponding 1H-2-thiopyridon-1-yl radical (for example with $P_2S_5$ or with Lawesson's reagent in toluene).

Nitration is effected under customary conditions, for example with a mixture of concentrated $HNO_3$ and concentrated $H_2SO_4$ at temperatures between 0° and 30°. Nitration takes place predominantly on the radical $R^5$; otherwise, as a rule mixtures in which the nitro groups can be on the radical $R^5$ or on the azachroman ring are obtained.

Similar methods apply to the halogenation, which can be carried out, for example, with elemental chlorine or bromine in one of the customary inert solvents at temperatures between about 0° and 30°.

An OH group can be converted into the corresponding alkoxy group by treatment with alkylating agents. Examples of suitable alkylating agents are compounds of the formula A-Cl, A-Br or A-I or corresponding sulfuric acid esters or sulfonic acid esters, such as methyl chloride, bromide or iodide, dimethyl sulfate and methyl p-toluenesulfonate. The alkylation is advantageously carried out in the presence or absence of one of the inert solvents mentioned, for example DMF, at temperatures between about 0° and about 120°, it also being possible for a catalyst to be present, preferably a base, such as potassium tert.-butylate or NaH.

Suitable acylating agents for acylation of amino or hydroxyl groups are advantageously the halides (for example chlorides or bromides) or anhydrides of carboxylic acids of the formula Ac-OH, for example acetic anhydride, propionyl chloride, isobutyryl bromide, formic acid/acetic anhydride or benzoyl chloride. The addition of a base, such as pyridine or triethylamine, during the acylation is possible. The acylation is advantageously carried out in the presence or absence of an inert solvent, for example a hydrocarbon, such as toluene, a nitrile, such as acetonitrile, an amide, such as DMF, or an excess of a tertiary base, such as pyridine or triethylamine, at temperatures between about 0° and about 160°, preferably between 20° and 120°. Formylation is also effected with formic acid in the presence of pyridine.

A base of the formula I can be converted into the associated acid addition salt with an acid. Possible acids for this reaction are, in particular, those which givee physiologically acceptable salts. It is thus possible to use inorganic acids, for example sulfuric acid, nitric acid, hydrohalic acids, such as hydrochloric acid or hydrobromic acid, phosphoric acids, such as orthophosphoric acid, or sulfamic acid, and furthermore organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalene-mono- and -disulfonic acids and laurylsulfuric acid. Salts with physiologically unacceptable acids, for example picrates, can be used to purify the compounds of the formula I.

The compounds of the formula I can have one or more chiral centres. During their preparation, they can therefore be obtained as racemates, or, if optically active starting substances are used, also in optically active form. If the compounds have two or more chiral centres, they can be obtained during synthesis as mixtures of racemates, from which the individual racemates can be isolated in a pure form, for example by recrystallization from inert solvents. Thus, for example, compounds of the formula I in which $R^1=R^2$, $R^3$ is OH and $R_4$ is H have two chiral centres. However, in the preparation by reaction of II with III, only a racemate with the trans-position of the substituents $R^3=OH$ and $R^5$ is quite predominantly formed. If desired, racemates obtained can be separated into their enantiomers mechanically or chemically by methods which are known per se. Diastereomers can thus be formed from the racemate by reaction with an optically active resolving agent. Suitable resolving agents for basic compounds of the formula I are, for example, optically active acids, such as the p- and L-forms of tartaric acid, dibenzoyltartaric acid, diacetyltartaric acid, camphorsulfonic acids, mandelic acid, malic acid or lactic acid. Carbinols (I, $R^3=OH$) can furthermore be esterified with the aid of chiral acylating reagents, for example D- or L-α-methylbenzyl isocyanate, and then resolved (compare European Patent A1-120,428). The various forms of the diastereomers can be resolved in a manner which is known per se, for example by fractional crystallization, and the enantiomers of the formula I can be liberated from the diastereomers in a manner which is known per se. Enantiomer resolutions are furthermore effected by chromatography on optically active carrier materials.

The compounds of the formula I and their physiologically acceptable salts can be used for the preparation of pharmaceutical formulations, in particular by a nonchemical route. They can thereby be brought into a suitable dosage form together with at least one solid, liquid and/or semi-liquid excipient or auxiliary and if appropriate in combination with one or more other active compound(s).

The invention furthermore relates to agents, in particular pharmaceutical formulations, containing at least one compound of the formula I and/or one of its physiologically acceptable salts.

These formulations can be used as medicaments in human or veterinary medicine. Possible excipients are organic or inorganic substances which are suitable for enteral (for example oral), parenteral or topical administration and do not react with the new compounnds, for example water, vegetable oils, benzyl alcohols, polyethylene glycols, glycerol triacetate, gelatine, carbohydrates, such as lactose or starch, magnesium stearate, talc, lanolin and vaseline. Tablets, coated tablets, capsules, syrups, elixirs or drops are particularly suitable for oral use, suppositories are suitable for rectal use, solutions, preferably oily or aqueous solutions, and furthermore suspensions, emulsions or implants are suitable for parenteral use, and ointments, creams, pastes, lotions, gels, sprays, foams, aerosols, solutions (f.e. in alcohols such as ethanol or isopropanol, acetonitrile, DMF, dimethylacetamide, 1,2-propanediol or their mixtures with one another or with water) or powders are suitable for topical use. The new compounds can also be lyophilized and the resulting lyophilisates can be used, for example, to prepare injection preparations. Liposomal preparations may also be considered, particularly for topical application. The formulations mentioned can be sterilized and/or can contain auxiliaries, such as lubricants, preservatives, stabilizers and/or wetting agents, emulsifiers, salts for influencing the osmotic pressure, buffer substances dyestuffs and flavor and/or aromatic substances. If desired, they can also contain one or more other active compounds, for example one or more vitamins.

The compounds of the formula I and their physiologically acceptable salts can be administered to humans or animals, in particular mammals, such as monkeys, dogs, cats, rats or mice, and can be used in the therapeutic treatment of the human or animal body and in combating diseases, in particular in the theray and/or prophylaxis of disturbances of the cardiovascular system, in particular decompensated cardiac insufficiency, angina pectoris, arrhythmia, peripheral or cerebral vascular diseases and disease conditions associated with high blood pressure, furthermore disease conditions associated with changes of the non-vascular muscular system, f.e. asthma, incontinence of the urinary bladder.

The substances according to the invention are thereby as a rule administered analogously to known antianginal and antihypertensive agents, for example nicorandil or BRL-34915 [2,2-dimethyl-4-(2-oxo-1-pyrrolidinyl)-6-cyano-chroman-3-ol; compare European Patent A1-173,848], preferably in dosages of between about 0.1 and 50 mg, in particular between 0.2 and 5 mg, per dosage unit. The daily dosage is preferably between about 0.001 and 1, in particular between 0.003 and 0.1 mg/kg of body weight. However, the specific dose for each particular patient depends on diverse factors, for example on the activity of the specific compound used and on the age, body weight, general state of health, sex, diet, administration time and route, rate of excretion, drug combination and severity of the particular disease to which the theray applies. Oral administration is preferred.

The compounds of formula I and their salts are, furthermore, suitable for the treatment of alopecia including androgenic alopecia and alopecia areata, particularly when applied topically. Pharmaceutical preparations are used especially for this purpose which are suitable for topical administration of the human scalp and which are cited above. They contain about 0.005 to 10, preferably 0.5 to 3 percent by weight of at least one compound of formula I and/or at least one of its salts. Otherwise, these compounds can be used against alopecia analogously to the informationn contained in WO 88/00822.

A preferred daily dosage range for the treatment of angina pectoris is 0.003 to 0.03 mg/kg of body weight.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, and of corresponding German application No. P.37 32 146.3 (the priority document), are hereby incorporated by reference.

EXAMPLES

In the following examples, "customary working up" means:

Water is added if necessary, the mixture is extracted with an organic solvent, such as ethyl acetate, the organic phase is separated off, dried over sodium sulfate, filtered and evaporated and the residue is purified by chromatography and/or crystallization.

All the temperatures above and below are stated in °C.

EXAMPLE 1

A mixture of 1.77 g of 2,2-dimethyl-3,4-epoxy-6-azachroman ("IIa"; compare European Patent A1-205,292), 1.5 g of 1H-2-pyridone ("pyridone"), 6 ml of ethanol and 0.6 ml of pyridine is boiled for 2 hours. The mixture is evaporated and the residue is chromatographed over silica gel. Trans-2,2-dimethyl-4-(1H-2-pyridon-1-yl)-6-azachroman-3-ol ("A") is eluted with ethyl acetate/methanol (95:5).

Melting point 208°–210°.

The trans-epimers of the following 6-azachroman-3-ols are obtained analogously:

2-Methyl-4-(1H-2-pyridon-1-yl)-
2,2-Dimethyl-4-(1H-2-thiopyridon-1-yl)
2,2-Dimethyl-4-(1H-6-methyl-2-pyridon-1-yl)-
2,2-Dimethyl-4-(1H-3-fluoro-2-pyridon-1-yl)-
2,2-Dimethyl-4-(1H-3-chloro-2-pyridon-1-yl)-
2,2-Dimethyl-4-(1H-5-chloro-2-pyridon-1-yl)-
2,2-Dimethyl-4-(1H-6-chloro-2-pyridon-1-yl)-
2,2-Dimethyl-4-(1H-3-hydroxy-2-pyridon-1-yl)-
2,2-Dimethyl-4-(1H-4-hydroxy-2-pyridon-1-yl)-, m.p. 208°–210°
2,2-Dimethyl-4-(1H-5-hydroxy-2-pyridon-1-yl)-, m.p. 207°–208°
2,2-Dimethyl-4-(1H-3-methoxy-2-pyridon-1-yl)-
2,2-Dimethyl-4-(1H-5-methoxy-2-pyridon-1-yl)-
2,2-Dimethyl-4-(1H-3-acetoxy-2-pyridon-1-yl)-
2,2-Dimethyl-4-(1H-3-nitro-2-pyridon-1-yl)-
2,2-Dimethyl-4-(1H-5-nitro-2-pyridon-1-yl)-
2,2-Dimethyl-4-(1H-3-amino-2-pyridon-1-yl)-
2,2-Dimethyl-4-(1H-5-amino-2-pyridon-1-yl)-
2,2-Dimethyl-4-(1H-3-acetamido-2-pyridon-1-yl)-
2,2-Dimethyl-4-(1H-5-acetamido-2-pyridon-1-yl)-
2,2-Dimethyl-4-(1H-3-carboxy-2-pyridon-1-yl)-
2,2-Dimethyl-4-(1H-5-carboxy-2-pyridon-1-yl)-
2,2-Dimethyl-4-(1H-5-methoxycarbonyl-2-pyridon-1-yl)-
2,2-Dimethyl-4-(1H-3,5-dichloro-2-pyridon-1-yl)-
2,2-Dimethyl-4-(1H-3,5-dibromo-2-pyridon-1-yl)-
2,2-Dimethyl-4-(1H-3,5-diiodo-2-pyridon-1-yl)-

2,2-Dimethyl-4-(1H-3-chloro-5-nitro-2-pyridon-1-yl)-
2,2-Dimethyl-4-(1H-3-nitro-5-chloro-2-kpyridon-1-yl)-
2,2-Dimethyl-4-(1H-3-bromo-5-nitro-2-pyridon-1-yl)-
2,2-Dimethyl-4-(1H-3-nitro-5-bromo-2-pyridon-1-yl)-
2,2-Dimethyl-4-(1H-3,5-dinitro-2-pyridon-1-yl)-
2,2-Dimethyl-4-(1H-3-chloro-5-amino-2-pyridon-1-yl)-
2,2-Dimethyl-4-(1H-3-amino-5-chloro-2-pyridon-1-yl)-
2,2-Dimethyl-4-(1H-3-bromo-5-amino-2-pyridon-1-yl)-
2,2-Dimethyl-4-(1H-3-amino-5-bromo-2-pyridon-1-yl)-
2,2-Dimethyl-4-(1H-3-chloro-5-acetamido-2-pyridon-1-yl)-
2,2-Dimethyl-4-(1H-3-acetamido-5-chloro-2-pyridon-1-yl)-
2,2-Dimethyl-4-(1H-3-bromo-5-acetamido-2-pyridon-1-yl)-
2,2-Dimethyl-4-(1H-acetamido-5-bromo-2-pyridon-1-yl)-
2,2-Ethyl-2-methyl-4-(1H-2-pyridon-1-yl)-
2,2-Diethyl-4-(1H-2-pyridon-1-yl)-
2,2-Trimethylene-4-(1H-2-pyridon-1-yl)-
2,2-Tetramethylene-4-(1H-2-pyridon-1-yl)-
2,2-Pentamethylene-4-(1H-2-pyridon-1-yl)-
2,2-Hexamethylene-4-(1H-2-pyridon-1-yl)-
2,2-Dimethyl-4-(1H-2-pyridazinon-1-yl)-
2,2-Dimethyl-4-(4,5-dihydro-1H-6-pyridazinon-1-yl)-
2,2-Dimethyl-4-(1H-3-hydroxy-6-pyridazinon-1-yl)-, m.p. 235°-235°
2,2-Dimethyl-4-(1H-3-ethoxycarbonyl-6-pyridazinon-1-yl)-
2,2-Dimethyl-4-(1H-2-pyrimidinon-1-yl)-
2,2-Dimethyl-4-(1H-4-hydroxy-2-pyrimidinon-1-yl)-
2,2-Dimethyl-4-(1H-6-pyrimidinon-1-yl)-
2,2-Dimethyl-4-(1H-4-hydroxy-6-pyrimidinon-1-yl)-
2,2-Dimethyl-4-(1H-2-pyrazinon-1-yl)-, m.p. 268°-272°.

EXAMPLE 2

Analogously to Example 1, trans-2,2-dimethyl-4-(1H-2-pyridon-1-yl)-5-azachroman-3-ol (m.p. 244°-246°) is obtained from 2,2-dimethyl-3,4-epoxy-5-azachroman [obtainable by condensation of 2-acetyl-3-hydroxypyridine with acetone to give 2,2-dimethyl-5-azachroman-4-one (melting point 102°-103°), reduction with NaBH4 to give 2,2-dimethyl-5-azachroman-4-ol (melting point 65°-67°), dehydration to give 2,2-dimethyl-5-aza-2H-chromene and epoxidization].

The trans-epimers of the following 5-azachroman-3-ols are obtained analogously:
2,2-Dimethyl-4-(1H-2-thiopyridon-1-yl)-
2,2-Dimethyl-4-(1H-3-chloro-2-pyridon-1-yl)-
2,2-Dimethyl-4-(1H-5-chloro-2-pyridon-1-yl)-
2,2-Dimethyl-4-(1H-6-chloro-2-pyridon-1-yl)-
2,2-Dimethyl-4-(1H-3-hydroxy-2-pyridon-1-yl)-
2,2-Dimethyl-4-(1H-4-hydroxy-2-pyridon-1-yl)-
2,2-Dimethyl-4-(1H-5-hydroxy-2-pyridon-1-yl)-
2,2-Dimethyl-4-(1H-3-methoxy-2-pyridon-1-yl)-
2,2-Dimethyl-4-(1H-3-acetoxy-2-pyridon-1-yl)-
2,2-Dimethyl-4-(1H-3-nitro-2-pyridon-1-yl)-
2,2-Dimethyl-4-(1H-5-nitro-2-pyridon-1-yl)-
2,2-Dimethyl-4-(1H-3-amino-2-pyridon-1-yl)-
2,2-Dimethyl-4-(1H-5-amino-2-pyridon-1-yl)-
2,2-Dimethyl-4-(1H-3-acetamido-2-pyridon-1-yl)-
2,2-Dimethyl-4-(1H-5-acetamido-2-pyridon-1-yl)-
2,2-Dimethyl-4-(1H-3-carboxy-2-pyridon-1-yl)-
2,2-Dimethyl-4-(1H-5-carboxy-2-pyridon-1-yl)-
2,2-Dimethyl-4-(1H-3,5-dichloro-2-pyridon-1-yl)-
2,2-Dimethyl-4-(1H-3,5-dibromo-2-pyridon-1-yl)-
2,2-Dimethyl-4-(1H-3-chloro-5-nitro-2-pyridon-1-yl)-
2,2-Dimethyl-4-(1H-3-nitro-5-chloro-2-pyridon-1-yl)-
2,2-Dimethyl-4-(1H-3-bromo-5-nitro-2-pyridon-1-yl)-
2,2-Dimethyl-4-(1H-3-nitro-5-bromo-2-pyridon-1-yl)-
2,2-Dimethyl-4-(1H-3,5-dinitro-2-pyridon-1-yl)-
2,2-Dimethyl-4-(1H-3-chloro-5-amino-2-pyridon-1-yl)-
2,2-Dimethyl-4-(1H-3-amino-5-chloro-2-pyridon-1-yl)-
2,2-Dimethyl-4-(1H-3-bromo-5-amino-2-pyridon-1-yl)-
2,2-Dimethyl-4-(1H-3-amino-5-bromo-2-pyridon-1-yl)-
2,2-Dimethyl-4-(1H-3-chloro-5-acetamido-2-pyridon-1-yl)-
2,2-Dimethyl-4-(1H-3-acetamido-5-chloro-2-pyridon-1-yl)-
2,2-Dimethyl-4-(1H-3-bromo-5-acetamido-2-pyridon-1-yl)-
2,2-Dimethyl-4-(1H-3-acetamido-5-bromo-2-pyridon-1-yl)-
2,2-Tetramethylene-4-(1H-2-pyridon-1-yl)-
2,2-Pentamethylene-4-(1H-2-pyridon-1-yl)-
2,2-Dimethyl-4-(1H-2-pyridazinon-1-yl)-
2,2-Dimethyl-4-(4,5-dihydro-1H-6-pyridazinon-1-yl)-
2,2-Dimethyl-4-(1H-3-hydroxy-6-pyridazinon-1-yl)-, m.p. 132°-133°
2,2-Dimethyl-4-(1H-3-ethoxycarbonyl-6-pyridazinon-1-yl)-
2,2-Dimethyl-4-(1H-2-pyrimidinon-1-yl)-
2,2-Dimethyl-4-(1H-4-hydroxy-2-pyrimidinon-1-yl)-
2,2-Dimethyl-4-(1H-6-pyrimidinon-1-yl)-
2,2-Dimethyl-4-(1H-4-hydroxy-6-pyrimidinon-1-yl)-
2,2-Dimethyl-4-(1H-2-pyrazinon-1-yl)-.

EXAMPLE 3

Analogously to Example 1, trans-2,2-dimethyl-4-(1H-2-pyridon-1-yl)-7-azachroman-3-ol is obtained from 2,2-dimethyl-3,4-epoxy-7-azachroman [obtainable by condensation of 4-acetyl-3-hydroxypyridine with acetone to give 2,2-dimethyl-7-azachroman-4-one (melting point 110°-112°), reduction with NaBH4 to give 2,2-dimethyl-7-azachroman-4-ol, dehydration to give 2,2-dimethyl-7-aza-2H-chromene and epoxidization].

The trans-epimers of the following 7-azachroman-3-ols are obtained analogously:
2,2-Dimethyl-4-(1H-2-thiopyridon-1-yl)-
2,2-Dimethyl-4-(1H-3-chloro-2-pyridon-1-yl)-
2,2-Dimethyl-4-(1H-5-chloro-2-pyridon-1-yl)-
2,2-Dimethyl-4-(1H-6-chloro-2-pyridon-1-yl)-
2,2-Dimethyl-4-(1H-3-hydroxy-2-pyridon-1-yl)-
2,2-Dimethyl-4-(1H-4-hydroxy-2-pyridon-1-yl)-
2,2-Dimethyl-4-(1H-5-hydroxy-2-pyridon-1-yl)-
2,2-Dimethyl-4-(1H-3-methoxy-2-pyridon-1-yl)-
2,2-Dimethyl-4-(1H-3-acetoxy-2-pyridon-1-yl)-
2,2-Dimethyl-4-(1H-3-nitro-2-pyridon-1-yl)-
2,2-Dimethyl-4-(1H-5-nitro-2-pyridon-1-yl)-
2,2-Dimethyl-4-(1H-3-amino-2-pyridon-1-yl)-
2,2-Dimethyl-4-(1H-5-amino-2-pyridon-1-yl)-
2,2-Dimethyl-4-(1H-3-acetamido-2-pyridon-1-yl)-
2,2-Dimethyl-4-(1H-5-acetamido-2-pyridon-1-yl)-
2,2-Dimethyl-4-(1H-3-carboxy-2-pyridon-1-yl)-
2,2-Dimethyl-4-(1H-5-carboxy-2-pyridon-1-yl)-
2,2-Dimethyl-4-(1H-3,5-dichloro-2-pyridon-1-yl)-
2,2-Dimethyl-4-(1H-3,5-dibromo-2-pyridon-1-yl)-
2,2-Dimethyl-4-(1H-3-chloro-5-nitro-2-pyridon-1-yl)-
2,2-Dimethyl-4-(1H-3-nitro-5-chloro-2-pyridon-1-yl)-
2,2-Dimethyl-4-(1H-3-bromo-5-nitro-2-pyridon-1-yl)-
2,2-Dimethyl-4-(1H-3-nitro-5-bromo-2-pyridon-1-yl)-
2,2-Dimethyl-4-(1H-3,5-dinitro-2-pyridon-1-yl)-
2,2-Dimethyl-4-(1H-3-chloro-5-amino-2-pyridon-1-yl)-
2,2-Dimethyl-4-(1H-3-amino-5-chloro-2-pyridon-1-yl)-
2,2-Dimethyl-4-(1H-3-bromo-5-amino-2-pyridon-1-yl)-
2,2-Dimethyl-4-(1H-3-amino-5-bromo-2-pyridon-1-yl)-

2,2-Dimethyl-4-(1H-3-chloro-5-acetamido-2-pyridon-1-yl)-
2,2-Dimethyl-4-(1H-3-acetamido-5-chloro-2-pyridon-1-yl)-
2,2-Dimethyl-4-(1H-3-bromo-5-acetamido-2-pyridon-1-yl)-
2,2-Dimethyl-4-(1H-3-acetamido-5-bromo-2-pyridon-1-yl)-
2,2-Tetramethylene-4-(1H-2-pyridon-1-yl)-
2,2-Pentamethylene-4-(1H-2-pyridon-1-yl)-
2,2-Dimethyl-4-(1H-2-pyridazinon-1-yl)-
2,2-Dimethyl-4-(4,5-dihydro-1H-6-pyridazinon-1-yl)-
2,2-Dimethyl-4-(1H-3-hydroxy-6-pyridazinon-1-yl)-
2,2-Dimethyl-4-(1H-3-ethoxycarbonyl-6-pyridazinon-1-yl)-
2,2-Dimethyl-4-(1H-2-pyrimidinon-1-yl)-
2,2-Dimethyl-4-(1H-4-hydroxy-2-pyrimidinon-1-yl)-
2,2-Dimethyl-4-(1H-6-pyrimidinon-1-yl)-
2,2-Dimethyl-4-(1H-4-hydroxy-6-pyrimidinon-1-yl)-
2,2-Dimethyl-4-(1H-2-pyrazinon-1-yl)-.

EXAMPLE 4

Analogously to Example 1, trans-2,2-dimethyl-4-(1H-2-pyridon-1-yl)-8-azachroman-3-ol (m.p. 179°–180°) is obtained from 2,2-dimethyl-3,4-epoxy-8-azachroman [obtainable by condensation of 3-acetyl-2-hydroxypyridine with acetone to give 2,2-dimethyl-8-azachroman-4-one, reduction with NaBH₄ to give 2,2-dimethyl-8-azachroman-4-ol, dehydration to give 2,2-dimethyl-8-aza-2H-chromene and epoxidization].

The trans-epimers of the following 8-azachroman-3-ols are obtained analogously:
2,2-Dimethyl-4-(1H-2-thiopyridon-1-yl)-
2,2-Dimethyl-4-(1H-3-chloro-2-pyridon-1-yl)-
2,2-Dimethyl-4-(1H-5-chloro-2-pyridon-1-yl)-
2,2-Dimethyl-4-(1H-6-chloro-2-pyridon-1-yl)-
2,2-Dimethyl-4-(1H-3-hydroxy-2-pyridon-1-yl)-
2,2-Dimethyl-4-(1H-4-hydroxy-2-pyridon-1-yl)-
2,2-Dimethyl-4-(1H-5-hydroxy-2-pyridon-1-yl)-
2,2-Dimethyl-4-(1H-3-methoxy-2-pyridon-1-yl)-
2,2-Dimethyl-4-(1H-3-acetoxy-2-pyridon-1-yl)-
2,2-Dimethyl-4-(1H-3-nitro-2-pyridon-1-yl)-
2,2-Dimethyl-4-(1H-5-nitro-2-pyridon-1-yl)-
2,2-Dimethyl-4-(1H-3-amino-2-pyridon-1-yl)-
2,2-Dimethyl-4-(1H-5-amino-2-pyridon-1-yl)-
2,2-Dimethyl-4-(1H-3-acetamido-2-pyridon-1-yl)-
2,2-Dimethyl-4-(1H-5-acetamido-2-pyridon-1-yl)-
2,2-Dimethyl-4-(1H-3-carboxy-2-pyridon-1-yl)-
2,2-Dimethyl-4-(1H-5-carboxy-2-pyridon-1-yl)-
2,2-Dimethyl-4-(1H-3,5-dichloro-2-pyridon-1-yl)-
2,2-Dimethyl-4-(1H-3,5-dibromo-2-pyridon-1-yl)-
2,2-Dimethyl-4-(1H-3-chloro-5-nitro-2-pyridon-1-yl)-
2,2-Dimethyl-4-(1H-3-nitro-5-chloro-2-pyridon-1-yl)-
2,2-Dimethyl-4-(1H-3-bromo-5-nitro-2-pyridon-1-yl)-
2,2-Dimethyl-4-(1H-3-nitro-5-bromo-2-pyridon-1-yl)-
2,2-Dimethyl-4-(1H-3,5-dinitro-2-pyridon-1-yl)-
2,2-Dimethyl-4-(1H-3-chloro-5-amino-2-pyridon-1-yl)-
2,2-Dimethyl-4-(1H-3-amino-5-chloro-2-pyridon-1-yl)-
2,2-Dimethyl-4-(1H-3-bromo-5-amino-2-pyridon-1-yl)-
2,2-Dimethyl-4-(1H-3-amino-5-bromo-2-pyridon-1-yl)-
2,2-Dimethyl-4-(1H-3-chloro-5-acetamido-2-pyridon-1-yl)-
2,2-Dimethyl-4-(1H-3-acetamido-5-chloro-2-pyridon-1-yl)-
2,2-Dimethyl-4-(1H-3-bromo-5-acetamido-2-pyridon-1-yl)-
2,2-Dimethyl-4-(1H-3-acetamido-5-bromo-2-pyridon-1-yl)-
2,2-Tetramethylene-4-(1H-2-pyridon-1-yl)-
2,2-Pentamethylene-4-(1H-2-pyridon-1-yl)-
2,2-Dimethyl-4-(1H-2-pyridazinon-1-yl)-
2,2-Dimethyl-4-(4,5-dihydro-1H-6-pyridazinon-1-yl)-
2,2-Dimethyl-4-(1H-3-hydroxy-6-pyridazinon-1-yl)-
2,2-Dimethyl-4-(1H-3-ethoxycarbonyl-6-pyridazinon-1-yl)-
2,2-Dimethyl-4-(1H-2-pyrimidinon-1-yl)-
2,2-Dimethyl-4-(1H-4-hydroxy-2-pyrimidinon-1-yl)-
2,2-Dimethyl-4-(1H-6-pyrimidinon-1-yl)-
2,2-Dimethyl-4-(1H-4-hydroxy-6-pyrimidinon-1-yl)-
2,2-Dimethyl-4-(1H-2-pyrazinon-1-yl)-.

EXAMPLE 5

463 mg of 80% pure NaH (in paraffin oil) are introduced into a solution of 2.1 g of "A" in 105 ml of DMF under N₂. The mixture is stirred at 70° for 2 hours, water is added dropwise at 5°–10° and the mixture is worked up in the customary manner to give 2,2-dimethyl-4-(1H-2-pyridon-1-yl)-6-aza-2H-chromene ("8"). Melting point 118°–120°.

The following compounds are obtained analogously by dehydration of the corresponding 5-, 6-, 7- or 8-azachroman-3-ols:
2,2-Dimethyl-4-(1H-2-pyridon-1-yl)-5-aza-2H-chromene, m.p. 147°–148°
2,2-Dimethyl-4-(1H-2-pyridon-1-yl)-7-aza-2-chromene
2,2-Dimethyl-4-(1H-2-pyridon-1-yl)-8-aza-2H-chromene
2,2-Dimethyl-4-(1H-2-thiopyridon-1-yl)-5-aza-2H-chromene
2,2-Dimethyl-4-(1H-2-thiopyridon-1-yl)-6-aza-2H-chromene
2,2-Dimethyl-4-(1H-2-thiopyridon-1-yl)-7-aza-2H-chromene
2,2-Dimethyl-4-(1H-2-thiopyridon-1-yl)-8-aza-2H-chromene
2,2-Dimethyl-4-(1H-3-chloro-2-pyridon-1-yl)-5-aza-2H-chromene
2,2-Dimethyl-4-(1H-3-chloro-2-pyridon-1-yl)-6-aza-2H-chromene
2,2-Dimethyl-4-(1H-3-chloro-2-pyridon-1-yl)-7-aza-2H-chromene
2,2-Dimethyl-4-(1H-3-chloro-2-pyridon-1-yl)-8-aza-2H-chromene
2,2-Dimethyl-4-(1H-5-chloro-2-pyridon-1-yl)-5-aza-2H-chromene
2,2-Dimethyl-4-(1H-5-chloro-2-pyridon-1-yl)-6-aza-2H-chromene
2,2-Dimethyl-4-(1H-5-chloro-2-pyridon-1-yl)-7-aza-2H-chromene
2,2-Dimethyl-4-(1H-5-chloro-2-pyridon-1-yl)-8-aza-2H-chromene
2,2-Dimethyl-4-(1H-6-chloro-2-pyridon-1-yl)-5-aza-2H-chromene
2,2-Dimethyl-4-(1H-6-chloro-2-pyridon-1-yl)-6-aza-2H-chromene
2,2-Dimethyl-4-(1H-6-chloro-2-pyridon-1-yl)-7-aza-2H-chromene
2,2-Dimethyl-4-(1H-6-chloro-2-pyridon-1-yl)-8-aza-2H-chromene
2,2-Dimethyl-4-(1H-3-hydroxy-2-pyridon-1-yl)-5-aza-2H-chromene
2,2-Dimethyl-4-(1H-3-hydroxy-2-pyridon-1-yl)-6-aza-2H-chromene
2,2-Dimethyl-4-(1H-3-hydroxy-2-pyridon-1-yl)-7-aza-2H-chromene 2,2-Dimethyl-4-(1H-3-hydroxy-2-pyridon-1-yl)-8-aza-2H-chromene
2,2-Dimethyl-4-(1H-4-hydroxy-2-pyridon-1-yl)-5-aza-2H-chromene
2,2-Dimethyl-4-(1H-4-hydroxy-2-pyridon-1-yl)-6-aza-2H-chromene
2,2-Dimethyl-4-(1H-4-hydroxy-2-pyridon-1-yl)-aza-2H-chromene
2,2-Dimethyl-4-(1H-4-hydrxoy-2-pyridon-1-yl)-8-aza-2H-chromene
2,2-Dimethyl-4-(1H-5-hydroxy-2-pyridon-1-yl)-5-aza-2H-chromene
2,2-Dimethyl-4-(1H-hydroxy-2-pyridon-1-yl)-6-aza-2H-chromene
2,2-Dimethyl-4-(1H-5-hydroxy-2-pyridon-1-yl)-7-aza-2H-chromene
2,2-Dimethyl-4-(1H-5-hydrxoy-2-pyridon-1-yl)-8-aza-2H-chromene
2,2-Dimethyl-4-(1H-3-methoxy-2-pyridon-1-yl)-5-aza-2H-chromene
2,2-Dimethyl-4-(1H-3-methoxy-2-pyridon-1-yl)-6-aza-2H-chromene
2,2-Dimethyl-4-(1H-3-methoxy-2-pyridon-1-yl)-7-aza-2H-chromene
2,2-Dimethyl-4-(1H-3-methoxy-2-pyridon-1-yl)-8-aza-2H-chromene
2,2-Dimethyl-4-(1H-3-acetoxy-2-pyridon-1-yl)-5-aza-2H-chromene
2,2-Dimethyl-4-(1H-3-acetoxy-2-pyridon-1-yl)-6-aza-2H-chromene
2,2-Dimethyl-4-(1H-3-acetoxy-2-pyridon-1-yl)-7-aza-2H-chromene
2,2-Dimethyl-4-(1H-3-acetoxy-2-pyridon-1-yl)-8-aza-2H-chromene
2,2-Dimethyl-4-(1H-3-nitro-2-pyridon-1-yl)-5-aza-2H-chromene
2,2-Dimethyl-4-(1H-3-nitro-2-pyridon-1-yl)-6-aza-2H-chromene
2,2-Dimethyl-4-(1H-3-nitro-2-pyridon-1-yl)-7-aza-2H-chromene
2,2-Dimethyl-4-(1H-3-nitro-2-pyridon-1-yl)-8-aza-2H-chromene
2,2-Dimethyl-4-(1H-5-nitro-2-pyridon-1-yl)-5-aza-2H-chromene
2,2-Dimethyl-4-(1H-5-nitro-2-pyridon-1-yl)-6-aza-2H-chromene
2,2-Dimethyl-4-(1H-5-nitro-2-pyridon-1-yl)-7-aza-2H-chromene
2,2-Dimethyl-4-(1H-5-nitro-2-pyridon-1-yl)-8-aza-2H-chromene
2,2-Dimethyl-4-(1H-3-amino-2-pyridon-1-yl)-5-aza-2H-chromene
2,2-Dimethyl-4-(1H-3-amino-2-pyridon-1-yl)-6-aza-2H-chromene
2,2-Dimethyl-4-(1H-3-amino-2-pyridon-1-yl)-7-aza-2H-chromene
2,2-Dimethyl-4-(1H-3-amino-2-pyridon-1-yl)-8-aza-2H-chromene
2,2-Dimethyl-4-(1H-5-amino-2-pyridon-1-yl)-5-aza-2H-chromene
2,2-Dimethyl-4-(1H-5-amino-2-pyridon-1-yl)-6-aza-2H-chromene
2,2-Dimethyl-4-(1H-5-amino-2-pyridon-1-yl)-7-aza-2H-chromene
2,2-Dimethyl-4-(1H-5-amino-2-pyridon-1-yl)-8aza-2H-chromene
2,2-Dimethyl-4-(1H-3-acetamido-2-pyridon-1-yl)-5-aza-2H-chromene
2,2-Dimethyl-4-(1H-3-acetamido-2-pyridon-1-yl)-6-aza-2H-chromene
2,2-Dimethyl-4-(1H-3-acetamido-2-pyridon-1-yl)-7-aza-2H-chromene
2,2-Dimethyl-4-(1H-3-acetamido-2-pyridon-1-yl)-8-aza-2H-chromene
2,2-Dimethyl-4-(1H-5-acetamido-2-pyridon-1-yl)-5-aza-2H-chromene
2,2-Dimethyl-4-(1H-5-acetamido-2-pyridon-1-yl)-6-aza-2H-chromene
2,2-Dimethyl-4-(1H-5-acetamido-2-pyridon-1-yl)-7-aza-2H-chromene
2,2-Dimethyl-4-(1H-5-acetamido-2-pyridon-1-yl)-8-aza-2H-chromene
2,2-Dimethyl-4-(1H-3-carboxy-2-pyridon-1-yl)-5-aza-2H-chromene
2,2-Dimethyl-4-(1H-3-carboxy-2-pyridon-1-yl)-6-aza-2H-chromene
2,2-Dimethyl-4-(1H-3-carboxy-2-pyridon-1-yl)-7-aza-2H-chromene
2,2-Dimethyl-4-(1H-3-carboxy-2-pyridon-1-yl)-8-aza-2H-chromene
2,2-Dimethyl-4-(1H-5-carboxy-2-pyridon-1-yl)-5-aza-2H-chromene
2,2-Dimethyl-4-(1H-5-carboxy-2-pyridon-1-yl)-6-aza-2H-chromene
2,2-Dimethyl-4-(1H-5-carboxy-2-pyridon-1-yl)-7-aza-2H-chromene
2,2-Dimethyl-4-(1H-5-carboxy-2-pyridon-1-yl)-8-aza-2H-chromene
2,2-Dimethyl-4-(1H-3,5-dichloro-2-pyridon-1-yl)-5-aza-2H-chromene
2,2-Dimethyl-4-(1H-3,5-dichloro-2-pyridon-1-yl)-6-aza-2H-chromene
2,2-Dimethyl-4-(1H-3,5-dichloro-2-pyridon-1-yl)-7-aza-2H-chromene
2,2-Dimethyl-4-(1H-3,5-dichloro-2-pyridon-1-yl)-8-aza-2H-chromene
2,2-Dimethyl-4-(1H-3,5-dibromo-2-pyridon-1-yl)-5-aza-2H-chromene
2,2-Dimethyl-4-(1H-3,5-dibromo-2-pyridon-1-yl)-6-aza-2H-chromene
2,2-Dimethyl-4-(1H-3,5-dibromo-2-pyridon-1-yl)-7-aza-2H-chromene
2,2-Dimethyl-4-(1H-3,5-dibromo-2-pyridon-1-yl)-8-aza-2H-chromene
2,2-Dimethyl-4-(1H-3-chloro-5-nitro-2-pyridon-1-yl)-5-aza-2H-chromene
2,2-Dimethyl-4-(1H-3-chloro-5-nitro-2-pyridon-1-yl)-6-aza-2H-chromene
2,2-Dimethyl-4-(1H-3-chloro-5-nitro-2-pyridon-1-yl)-7-aza-2H-chromene
2,2-Dimethyl-4-(1H-3-chloro-5-nitro-2-pyridon-1-yl)-8-aza-2H-chromene
2,2-Dimethyl-4-(1H-3-nitro-5-chloro-2-pyridon-1-yl)-5-aza-2H-chromene
2,2-Dimethyl-4-(1H-3-nitro-5-chloro-2-pyridon-1-yl)-6-aza-2H-chromene
2,2-Dimethyl-4-(1H-3-nitro-5-chloro-2-pyridon-1-yl)-7-aza-2H-chromene
2,2-Dimethyl-4-(1H-3-nitro-5-chloro-2-pyridon-1-yl)-8-aza-2H-chromene
2,2-Dimethyl-4-(1H-3-bromo-5-nitro-2-pyridon-1-yl)-5-aza-2H-chromene
2,2-Dimethyl-4-(1H-3-bromo-5-nitro-2-pyridon-1-yl)-6-aza-2H-chromene
2,2-Dimethyl-4-(1H-3-bromo-5-nitro-2-pyridon-1-yl)-7-aza-2H-chromene 2,2-Dimethyl-4-(1H-3-bromo-5-nitro-2-pyridon-1-yl)-8-aza-2H-chromene
2,2-Dimethyl-4-(1H-3-nitro-5-bromo-2-pyridon-1-yl)-5-aza-2H-chromene
2,2-Dimethyl-4-(1H-3-nitro-5-bromo-2-pyridon-1-yl)-6-aza-2H-chromene
2,2-Dimethyl-4-(1H-3-nitro-5-bromo-2-pyridon-1-yl)-7-aza-2H-chromene
2,2-Dimethyl-4-(1H-3-nitro-5-bromo-2-pyridon-1-yl)-8-aza-2H-chromene
2,2-Dimethyl-4-(1H-3,5-dinitro-2-pyridon-1-yl)-5-aza-2H-chromene
2,2-Dimethyl-4-(1H-3,5-dinitro-2-pyridon-1-yl)-6-aza-2H-chromene
2,2-Dimethyl-4-(1H-3,5-dinitro-2-pyridon-1-yl)-7-aza-2H-chromene
2,2-Dimethyl-4-(1H-3,5-dinitro-2-pyridon-1-yl)-8-aza-2H-chromene
2,2-Dimethyl-4-(1H-3-chloro-5-amino-2-pyridon-1-yl)-5-aza-2H-chromene
2,2-Dimethyl-4-(1H-3-chloro-5-amino-2-pyridon-1-yl)-6-aza-2H-chromene
2,2-Dimethyl-4-(1H-3-chloro-5-amino-2-pyridon-1-yl)-7-aza-2H-chromene
2,2-Dimethyl-4-(1H-3-chloro-5-amino-2-pyridon-1-yl)-8-aza-2H-chromene
2,2-Dimethyl-4-(1H-3-amino-5-chloro-2-pyridon-1-yl)-5-aza-2H-chromene
2,2-Dimethyl-4-(1H-3-amino-5-chloro-2-pyridon-1-yl)-6-aza-2H-chromene
2,2-Dimethyl-4-(1H-3-amino-5-chloro-2-pyridon-1-yl)-7-aza-2H-chromene
2,2-Dimethyl-4-(1H-3-amino-5-chloro-2-pyridon-1-yl)-8-aza-2H-chromene
2,2-Dimethyl-4-(1H-3-bromo-5-amino-2-pyridon-1-yl)-5-aza-2H-chromene
2,2-Dimethyl-4-(1H-3-bromo-5-amino-2-pyridon-1-yl)-6-aza-2H-chromene
2,2-Dimethyl-4-(1H-3-bromo-5-amino-2-pyridon-1-yl)-7-aza-2H-chromene
2,2-Dimethyl-4-(1H-3-bromo-5-amino-2-pyridon-1-yl)-8-aza-2H-chromene
2,2-Dimethyl-4-(1H-3-amino-5-bromo-2-pyridon-1-yl)-5-aza-2H-chromene
2,2-Dimethyl-4-(1H-3-amino-5-bromo-2-pyridon-1-yl)-6-aza-2H-chromene
2,2-Dimethyl-4-(1H-3-amino-5-bromo-2-pyridon-1-yl)-7-aza-2H-chromene
2,2-Dimethyl-4-(1H-3-amino-5-bromo-2-pyridon-1-yl)-8-aza-2H-chromene
2,2-Dimethyl-4-(1H-3-chloro-5-acetamido-2-pyridon-1-yl)-5-aza-2H-chromene
2,2-Dimethyl-4-(1H-3-chloro-5-acetamido-2-pyridon-1-yl)-6-aza-2H-chromene
2,2-Dimethyl-4-(1H-3-chloro-5-acetamido-2-pyridon-1-yl)-7-aza-2H-chromene
2,2-Dimethyl-4-(1H-3-chloro-5-acetamido-2-pyridon-1-yl)-8-aza-2H-chromene
2,2-Dimethyl-4-(1H-3-acetamido-5-chloro-2-pyridon-1-yl)-5-aza-2H-chromene
2,2-Dimethyl-4-(1H-3-acetamido-5-chloro-2-pyridon-1-yl)-6-aza-2H-chromene
2,2-Dimethyl-4-(1H-3-acetamido-5-chloro-2-pyridon-1-yl)-7-aza-2H-chromene
2,2-Dimethyl-4-(1H-3-acetamido-5-chloro-2-pyridon-1-yl)-8-aza-2H-chromene
2,2-Dimethyl-4-(1H-3-bromo-5-acetamido-2-pyridon-1-yl)-5-aza-2H-chromene
2,2-Dimethyl-4-(1H-3-bromo-5-acetamido-2-pyridon-1-yl)-6-aza-2H-chromene
2,2-Dimethyl-4-(1H-3-bromo-5-acetamido-2-pyridon-1-yl)-7-aza-2H-chromene
2,2-Dimethyl-4-(1H-3-bromo-5-acetamido-2-pyridon-1-yl)-8-aza-2H-chromene
2,2-Dimethyl-4-(1H-3-acetamido-5-bromo-2-pyridon-1-yl)-5-aza-2H-chromene
2,2-Dimethyl-4-(1H-3-acetamido-5-bromo-2-pyridon-1-yl)-6-aza-2H-chromene
2,2-Dimethyl-4-(1H-3-acetamido-5-bromo-2-pyridon-1-yl)-7-aza-2H-chromene
2,2-Dimethyl-4-(1H-3-acetamido-5-bromo-2-pyridon-1-yl)-8-aza-2H-chromene
2,2-Tetramethylene-4-(1H-2-pyridon-1-yl)-5-aza-2H-chromene
2,2-Tetramethylene-4-(1H-2-pyridon-1-yl)-6-aza-2H-chromene
2,2-Tetramethylene-4-(1H-2-pyridon-1-yl)-7-aza-2H-chromene
2,2-Tetramethylene-4-(1H-2-pyridon-1-yl)-8-aza-2H-chromene
2,2-Pentamethylene-4-(1H-2-pyridon-1-yl)-5-aza-2H-chromene
2,2-Pentamethylene-4-(1H-2-pyridon-1-yl)-6-aza-2H-chromene
2,2-Pentamethylene-4-(1H-2-pyridon-1-yl)-7-aza-2H-chromene
2,2-Pentamethylene-4-(1H-2-pyridon-1-yl)-8-aza-2H-chromene
2,2-Dimethyl-4-(1H-2-pyridazinon-1-yl)-5-aza-2H-chromene
2,2-Dimethyl-4-(1H-2-pyridazinon-1-yl)-6-aza-2H-chromene
2,2-Dimethyl-4-(1H-2-pyridazinon-1-yl)-7-aza-2H-chromene
2,2-Dimethyl-4-(1H-2-pyridazinon-1-yl)-8-aza-2H-chromene
2,2-Dimethyl-4-(4,5-dihydro-1H-6-pyridazinon-1-yl)-5-aza-2H-chromene
2,2-Dimethyl-4-(4,5-dihydro-1H-6-pyridazinon-1-yl)-6-aza-2H-chromene
2,2-Dimethyl-4-(4,5-dihydro-1H-6-pyridazinon-1-yl)-7-aza-2-H-chromene
2,2-Dimethyl-4-(4,5-dihydro-1H-6-pyridazinon-1-yl)-8-aza-2-H-chromene
2,2-Dimethyl-4-(1H-3-hydroxy-6-pyridazinon-1-yl)-5-aza-2H-chromene
2,2-Dimethyl-4-(1H-3-hydroxy-6-pyridazinon-1-yl)-6-aza-2H-chromene
2,2-Dimethyl-4-(1H-3-hydroxy-6-pyridazinon-1-yl)-7-aza-2H-chromene
2,2-Dimethyl-4-(1H-3-hydroxy-6-pyridazinon-1-yl)-8-aza-2H-chromene
2,2-Dimethyl-4-(1-H-3-ethoxycarbonyl-6-pyridazinon-1-yl)-5-aza-2H-chromene
2,2-Dimethyl-4-(1H-3-ethoxycarbonyl-6-pyridazinon-1-yl)-6-aza-2H-chromene
2,2-Dimethyl-4-(1H-3-ethoxycarbonyl-6-pyridazinon-1-yl)-7-aza-2H-chromene
2,2-Dimethyl-4-(1H-3-ethoxycarbonyl-6-pyridazinon-1-yl)-8-aza-2H-chromene
2,2-Dimethyl-4-(1H-2-pyrimidinon-1-yl)-5-aza-2H-chromene
2,2-Dimethyl-4-(1H-2-pyrimidinon-1-yl)-6-aza-2H-chromene
2,2-Dimethyl-4-(1H-2-pyrimidinon-1-yl)-7-aza-2H-chromene 2,2-Dimethyl-4-(1H-2-pyrimidinon-1-yl)-8-aza-2H-chromene
2,2-Dimethyl-4-(1H-4-hydroxy-2-pyrimidinon-1-yl)-5-aza-2H-chromene
2,2-Dimethyl-4- (1H-4-hydroxy-2-pyrimidinon-1-yl)-6-aza-2H-chromene
2,2-Dimethyl-4-(1H-4-hydroxy-2-pyrimidinon-1-yl)-7-aza-2H-chromene
2,2-Dimethyl-4-(1H-4-hydroxy-2-pyrimidinon-1-yl)-8-aza-2H-chromene
2,2-Dimethyl-4-(1H-6-pyrimidinon-1-yl)-5-aza-2H-chromene
2,2-Dimethyl-4-(1H-6-pyrimidinon-1-yl)-6-aza-2H-chromene
2,2-Dimethyl-4-(1H-6-pyrimidinon-1-yl)-7-aza-2H-chromene
2,2-Dimethyl-4-(1H-6-pyrimidinon-1-yl)-8-aza-2H-chromene
2,2-Dimethyl-4-(1H-6-hydroxy-2-pyrimidinon-1-yl)-5-aza-2H-chromene
2,2-Dimethyl-4-(1H-6-hydroxy-2-pyrimidinon-1-yl)-6-aza-2H-chromene
2,2-Dimethyl-4-(1H-6-hydroxy-2-pyrimidinon-1-yl)-7-aza-2H-chromene
2,2-Dimethyl-4-(1H-6-hydroxy-2-pyrimidinon-1-yl)-8-aza-2H-chromene
2,2-Dimethyl-4-(1H-2-pyrazinon-1-yl)-5-aza-2H-chromene
2,2-Dimethyl-4-(1H-2-pyrazinon-1-yl)-6-aza-2H-chromene
2,2-Dimethyl-4-(1H-2-pyrazinon-1-yl)-7-aza-2H-chromene
2,2-Dimethyl-4-(1H-2-pyrazinon-1-yl)-8-aza-2H-chromene.

EXAMPLE 6

0.4 g of a 60% strength oil dispersion of NaH are added to a solution of 2.82 g of trans-2,2-dimethyl-3-bromo-6-azachroman-4-ol in 15 ml of DMSO, with stirring. The mixture is stirred for 1 hour, 2,2-dimethyl-3,4-epoxy-6-azachroman being intermediately formed. 1.43 g of 1H-2-pyridone and a further 0.5 g of NaH dispersion are added and the mixture is stirred at 20° for 16 hours. Working up analogously to Example 1 gives "A", melting point 208°–210°.

EXAMPLE 7

A mixture of 2 g of "A", 11.7 ml of formic acid and 3.3 ml of acetic anhydride is left to stand at 20° for 16 hours and is then heated at 40°–42° for 2 hours. After evaporation and customary working up, 2,2-dimethyl-3-formyloxy-4-(1H-2-pyridon-1-yl)-6-azachroman is obtained.

EXAMPLE 8

A mixture of 1 g of "A" and 5 ml of acetic anhydride is boiled for 1 hour. The mixture is cooled and worked up in the customary manner to give 2,2-dimethyl-3-acetoxy-4-(1H-2-pyridon-1-yl)-6-azachroman.

EXAMPLE 9

2.96 g of "A" are suspended in 100 ml of water, and 3.2 g of bromine are added dropwise at 10°–20°, with stirring. The substance dissolves and 2,2-dimethyl-4-(1H-3,5-dibromo-2-pyridon-1-yl)-6-azachroman-3-ol precipitates out and is filtered off.

EXAMPLE 10

2.78 g of "B" are dissolved in a mixture of 10 ml of concentrated nitric acid (68% strength; D. 1.41) and 12 ml of concentrated sulfuric acid and the mixture is stirred at 20° for 3 hours, poured onto ice, filtered, and washed with water to give a mixture of 2,2-dimethyl-4-(1H-3- and -5-nitro-pyridon-1-yl)-6-aza-2H-chromene, which can be separated by chromatography.

EXAMPLE 11

A solution of 1 g of 2,2-dimethyl-4-(1H-3-nitro-2-pyridon-1-yl)-6-azachroman-3-ol in 25 ml of methanol is hydrogenated at 20° and 1 bar on 0.5 g of 5% strength Pd-C until the reaction stops. The mixture is filtered and the filtrate is evaporated to give 2,2-dimethyl-4-(1H-3-amino-2-pyridon-1-yl)-6-azachroman-3-ol.

EXAMPLE 12

A solution of 1 g of 2,2-dimethyl-4-(1H-3-amino-2-pyridon-1-yl)-6-aza-2H-chromene in 15 ml of HCOOH and 1 ml of pyridine is boiled for 19 hours and evaporated. Customary working up gives 2,2-dimethyl-4-(1H-3formamido -2-pyridon-1-yl)-6-aza-2H-chromene.

EXAMPLE 13

A mixture of 1 of 2,2-dimethyl-4-(1H-5-amino-2-pyridon-1-yl)-6-aza-2H-chromene, 10 ml of acetic anhydride and 10 ml of pyridine is left to stand at 20° for 16 hours. It is evaporated and the residue is purified by chromatography to give 2,2-dimethyl-4-(1H-5-acetamido-2-pyridon-1-yl)-6-aza-2H-chromene.

EXAMPLE 14

A mixture of 272 mg of "A", 808 mg of Lawesson's reagent and 50 ml of toluene is boiled under $N_2$ for 1 hour. Customary working up gives 2,2-dimethyl-4-(1H-2-thiopyridon-1-yl)-6-azachroman-3-ol.

2,2-Dimethyl-4-(1H-2-thiopyridon-1-yl)-6-aza-2H-chromene is obtained analogously from "B".

EXAMPLE 15

With stirring and under an $N_2$ atmosphere at 10°–15°, a solution of 4.66 g of hexachlorodisilan in 30 ml of chloroform is added dropwise to a suspension of 500 mg of 2,2-dimethyl-4-(1H-2-pyridon-1-yl)-7-azachroman-3-ol-7-N-oxide (obtainable from 2,2-dimethyl-3,4-epoxy-7-aza-chromane-7-N-oxide and pyridone) in 120 ml of chloroform. Stirring is continued for 1 hour at 20°, 36.4 ml of 10% aqueous sodium hydroxide is added dropwise at 0°–5°, the mixture is worked up as usual, and "A" is obtained; m.p. 208°–210°.

The following examples relate to pharmaceutical formulations which contain compounds of the formula I or their physiologically acceptable salts.

EXAMPLE A

Tablets

A mixture of 1 kg of 2,2-dimethyl-4-(1H-2-pyridon-1-yl)-6-aza-2H-chromene, 400 kg of lactose, 120 kg of potato starch, 20 kg of talc and 10 kg of magnesium stearate is pressed to tablets in the customary manner such that each tablet contains 1 mg of active compound.

EXAMPLE B

Coated tablets

Tablets are pressed analogously to Example A and are then coated in the customary manner with a coating of sucrose, potato starch, talc, tragacanth and dyestuff.

EXAMPLE C

Capsules

Hard gelatine capsules are filled with 1 kg of 2,2-dimethyl-4-(1H-2-pyridon-1-yl)-6-azachroman-3-ol in the customary manner so that each capsule contains 2 mg of active compound.

EXAMPLE D

Ampoules

A solution of 1 kg of 2,2-dimethyl-4-(1H-2-pyridon-1-yl)7-aza-2H-chromene in 1000 l of doubly-distilled water is subjected to sterile filtration and bottled in ampoules and subjected to sterile sealing. Each ampoule contains 1 mg of active compound.

EXAMPLE E

Solution for topical application (against alopecia)

A solution is prepared by dissolving 500 g of "A" (or "B") in a mixture of 5.2 kg of 1,2-propanediol and 15 l of ethanol. The solution is filled up with ethanol to a volume of 25 l, filtered under sterile conditions and filled into bottles.

EXAMPLE F

Gel

A mixture of 0.45 g Carbopol 934 P (=carboxyvinyl polymer) with 40 ml of doubly-distilled water and 27 ml of ethanol is prepared and a solution of 0.5 g of A" (or "B") and 0.45 g of diisopropanolamine in 10 ml of 1,2-propanediol and 13 ml of ethanol is added. The whole is thoroughly mixed, filled up with water to a volume of 100 ml and thoroughly mixed again. The gel obtained contains 0.5 percent by weight of active substance.

Tablets, coated tablets, capsules or ampoules which contain one or more of the other active compounds of the formula I and/or their physiologically acceptable salts can be obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An azachroman derivative of the formula

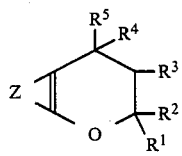

wherein

Z is
 (a) —N=CH—CH=CH—,
 (b) —CH=N—CH=CH—,
 (c) —CH=CH—N=CH— or
 (d) —CH=CH—CH=N—;
$R^1$ is A,
$R^2$ is H or A, or
$R^1$ and $R^2$ together are alkylene with 3-6 C atoms;
$R^3$ is OH or OAc,
$R^4$ is H, or
$R^3$ and $R^4$ together are a bond;
$R^5$ is 1H-2-pyridon-1-yl, 1H-6-pyridazinon-1-yl, 1H-2-pyrimidinon-1-yl, 1H-6-pyrimidinon-1-yl, 1H-2-pyrazinon-1-yl or 1H-2-thiopyridon-1-yl, or 1H-2-pyridon-1-yl, 1H-6-pyridazinon-1-yl, 1H-2-pyrimidinon-1-yl, 1H-6-pyrimidinon-1-yl, 1H-2-pyrazinon-1-yl or 1H-2-thiopyridon-1-yl mono- or disubstituted by A, F, Cl, Br, I, OH, OA, OAc, $NO_2$, $NH_2$, AcNH, HOOC or AOOC:
A is $C_{1-6}$-alkyl and
Ac is $C_{1-8}$-alkanoyl or $C_{7-11}$-aroyl; or a pharmaceutically acceptable salt thereof.

2. A compound according to claim 1 of the formula

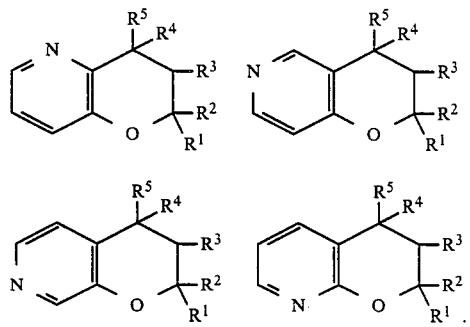

3. A compound according to claim 2, wherein A is $C_{1-4}$-alkyl.

4. A compound according to claim 2, wherein A is methyl.

5. A compound according to claim 2, wherein $R^1$ and $R^2$ are together —$(CH_2)_n$—, and n is 3-6.

6. A compound according to claim 2, wherein Ac is $C_{1-6}$-alkanoyl.

7. A compound according to claim 2, wherein Ac is formyl or acetyl.

8. A compound according to claim 2, wherein $R^1$ and $R^2$ are each methyl.

9. A compound according to claim 2, wherein $R^3$ and $R^4$ are together a single bond.

10. A compound according to claim 2, wherein $R^4$ is H and $R^3$ is OH, O—CHO or O—COCH$_3$.

11. A compound according to claim 2, wherein $R^5$ is 1H-2-pyridon-1-yl, 1H-2-pyrazinon-1-yl or 1H-4-hydroxy-2-pyridon-1-yl.

12. A compound according to claim 2, wherein $R^1$ and $R^2$ are each A.

13.
 (a) 2,2-Dimethyl-4-(1H-2-pyridon-1-yl)-5-azachroman-3-ol;
 (b) 2,2-Dimethyl-4-(1H-2-pyridon-1-yl)-5-aza-2H-chromene;
 (c) 2,2-Dimethyl-4-(1H-2-pyridon-1-yl)-6-azachroman-3-ol;
 (d) 2,2-Dimethyl-4-(1H-2-pyridon-1-yl)-6-aza-2H-chromene;

(e) 2,2-Dimethyl-4-(1H-2-pyridon-1-yl)-7-azachroman-3-ol;
(f) 2,2-Dimethyl-4-(1H-2-pyridon-1-yl)-7-aza-2H-chromene;
(g) 2,2-Dimethyl-4-(1H-2-pyridon-1-yl)-8-aza-2H-chroman-3-ol;
(h) 2,2-Dimethyl-4-(1H-2-pyridon-1-yl)-8-aza-2H-chromene, each a compound of claim 1.

14. A composition comprising a compound according to claim 1 and a pharmaceutically acceptable carrier.

* * * * *